United States Patent [19]

Parker et al.

[11] Patent Number: 5,405,985
[45] Date of Patent: Apr. 11, 1995

[54] PREPARATION OF SULFUR-CONTAINING ORGANOSILICON COMPOUNDS

[75] Inventors: Dane K. Parker, Massillon; Richard T. Musleve, Akron; Robert C. Hirst, Akron; Roger J. Hopper, Akron, all of Ohio

[73] Assignee: The Goodyear Tire & Rubber Company, Akron, Ohio

[21] Appl. No.: 272,366

[22] Filed: Jul. 8, 1994

[51] Int. Cl.$^6$ ................................................ C07F 7/08
[52] U.S. Cl. ................................................ 556/427
[58] Field of Search ........................................ 556/427

[56] References Cited

U.S. PATENT DOCUMENTS

| | | | |
|---|---|---|---|
| 3,842,111 | 10/1974 | Meyer-Simon et al. | 260/448.2 E |
| 3,873,489 | 3/1975 | Thurn et al. | 260/33.6 AQ |
| 3,978,103 | 8/1976 | Meyer-Simon et al. | 260/448.8 R |
| 3,997,581 | 12/1976 | Pietka et al. | 260/448.8 R |
| 4,129,585 | 12/1978 | Buder et al. | 260/448.8 R |
| 4,384,132 | 5/1983 | Schwarz et al. | 556/427 |
| 4,401,598 | 8/1983 | Karl et al. | 260/349 |
| 4,408,064 | 10/1983 | Schwarz et al. | 556/427 |
| 4,433,164 | 2/1984 | Jenck | 560/207 |
| 4,507,490 | 3/1985 | Panster et al. | 556/427 |
| 4,595,740 | 6/1986 | Panster | 556/427 X |
| 4,946,977 | 8/1990 | Bernhardt et al. | 556/440 |
| 5,110,969 | 5/1992 | Dittrich et al. | 556/427 |

FOREIGN PATENT DOCUMENTS

| | | |
|---|---|---|
| 0024926 | 8/1980 | European Pat. Off. . |
| 0029176 | 11/1980 | European Pat. Off. . |
| 0483479 | 8/1991 | European Pat. Off. . |
| 0483480 | 8/1991 | European Pat. Off. . |
| 1484909 | 9/1977 | United Kingdom . |

OTHER PUBLICATIONS

S Wolff, et al, Eur. Rubber J., 16, Jan. 1994.

K. E. Koenig, et al, Tet. Lett., 2275 (1974).

Primary Examiner—Paul F. Shaver
Attorney, Agent, or Firm—Bruce J. Hendricks

[57] ABSTRACT

The present invention relates to a process for the production of organosilicon compounds of the formula $$Z\text{-Alk-}S_n\text{-Alk-}Z \quad (I)$$

in which Z is selected from the group consisting of

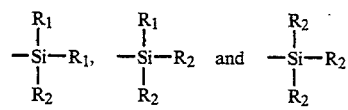

where $R_1$ is an alkyl group of 1 to 4 carbon atoms, cyclohexyl or phenyl;

$R_2$ is alkoxy of 1 to 8 carbon atoms, or cycloalkoxy of 5 to 8 carbon atoms;

Alk is a divalent hydrocarbon of 1 to 18 carbon atoms and n is an integer of 2 to 8; comprising reacting (A) a compound of the formula:

$$Z\text{-Alk-}X \quad (II)$$

when X is Cl, Br or I; with (B) a compound of the formula $$Me_2S_n \quad (III)$$

where Me is ammonium, or an alkali metal;
wherein the reaction is conducted in the presence of a phase transfer catalyst and an aqueous phase.

13 Claims, No Drawings

PREPARATION OF SULFUR-CONTAINING ORGANOSILICON COMPOUNDS

BACKGROUND

Sulfur containing organosilicon compounds are useful as reactive coupling agents between rubber and silica fillers providing for improved physical properties. They are also useful as adhesion primers for glass, metals and other substrates.

U.S. Pat. Nos. 3,842,111, 3873,489 and 3,978,103 disclose the preparation of various sulfur containing organosilicon compounds. These organosilicon compounds are prepared by reacting (1) 2 moles of a compound of the formula

Z-Alk-hal where hal is a chlorine, bromine or iodine; Z is

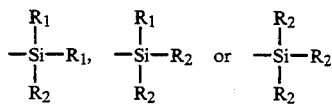

where $R_1$ is an alkyl of 1 to 4 carbon atoms or phenyl and $R_2$ is alkoxy of 1 to 8 carbon atoms, cycloalkoxy of 5 to 8 carbon atoms or alkylmercapto with 1 to 8 carbon atoms; Alk is a divalent aliphatic hydrocarbon or unsaturated hydrocarbon or a cyclic hydrocarbon containing 1 to 18 carbon atoms; with (2) 1 mole of a compound of the formula

Me$_2$S$_n$ where Me is ammonium or a metal atom and n is a whole number from 2 to 6. Since the two starting materials are liquid, the reaction can take place in the absence of a solvent; however, a volatile inert organic solvent is not only generally used but is preferred. The reaction is carried out with the exclusion of water. The reason for the exclusion of water is to avoid the alkaline hydrolysis reaction of the silyl alkoxy groups which will ultimately lead to insoluble polymeric by-products and lower the overall yield of desired product. Representative organic solvents include aliphatic alcohols such as methyl alcohol and ethyl alcohol. At the end of the reaction between the two starting materials, the separated salt is removed by filtration. The filtrate is then freed from the solvent by distillation under vacuum. Unfortunately, this process suffers from many practical problems. Many of these problems relate to the solvent, e.g. ethyl alcohol. Ethyl alcohol has a low flash point. In addition, it is difficult to obtain and maintain in the water-free (anhydrous) state.

SUMMARY OF THE INVENTION

The present invention relates to a process for the production of sulfur containing organosilicon compounds. The process involves reacting a haloalkylsilane compound with an ammonium polysulfide or metal polysulfide. Contrary to the previously described prior art anhydrous process, the process of the present invention is characterized by using an aqueous phase with a phase transfer catalyst.

DETAILED DESCRIPTION OF THE INVENTION

There is disclosed a process for the production of organosilicon compounds of the formula

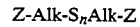

Z-Alk-S$_n$Alk-Z    (I)

in which Z is selected from the group consisting of

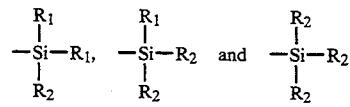

where $R_1$ is an alkyl group of 1 to 4 carbon atoms, cyclohexyl or phenyl;
$R_2$ is alkoxy of 1 to 8 carbon atoms, or cycloalkoxy of 5 to 8 carbon atoms;
Alk is a divalent hydrocarbon of 1 to 18 carbon atoms and n is an integer of 2 to 8; comprising reacting (A) a compound of the formula:

Z-Alk-X    (II)

when X is Cl, Br or I; with (B) a compound of the formula

Me$_2$S$_n$    (III)

where Me is ammonium, or an alkali metal;
wherein the reaction is conducted in the presence of a phase transfer catalyst and an aqueous phase.

Examples of sulfur containing organosilicon compounds which may be prepared in accordance with the present invention include:
3,3'-bis(trimethoxysilylpropyl)disulfide,
3,3'-bis(triethoxysilylpropyl)tetrasulfide,
3,3'-bis(triethoxysilylpropyl)octasulfide,
3,3'-bis(trimethoxysilylpropyl)tetrasulfide,
2,2'-bis(triethoxysilylethyl)tetrasulfide,
3,3'-bis(trimethoxysilylpropyl)trisulfide,
3,3'-bis(triethoxysilylpropyl)trisulfide,
3,3'-bis(tributoxysilylpropyl)disulfide,
3,3'-bis(trimethoxysilylpropyl)hexasulfide,
3,3'-bis(trimethoxysilylpropyl)octasulfide,
3,3'-bis(trioctoxysilylpropyl)tetrasulfide,
3,3'-bis(trihexoxysilylpropyl)disulfide,
3,3'-bis(tri-2''-ethylhexoxysilylpropyl)trisulfide,
3,3'-bis(triisooctoxysilylpropyl)tetrasulfide,
3,3'-bis(tri-t-butoxysilylpropyl)disulfide,
2,2'-bis(methoxy diethoxy silyl ethyl)tetrasulfide,
2,2'-bis(tripropoxysilylethyl)pentasulfide,
3,3'-bis(tricyclonexoxysilylpropyl)tetrasulfide,
3,3'-bis(tricyclopentoxysilylpropyl)trisulfide,
2,2'-bis(tri-2''-methylcyclohexoxysilylethyl)tetrasulfide,
bis(trimethoxysilylmethyl)tetrasulfide,
3-methoxy ethoxy propoxysilyl 3'-diethoxybutoxysilylpropyltetrasulfide,
2,2'-bis(dimethyl methoxysilylethyl)disulfide,
2,2'-bis(dimethyl sec.butoxysilylethyl)trisulfide,
3,3'-bis(methyl butylethoxysilylpropyl)tetrasulfide,
3,3'-bis(di t-butylmethoxysilylpropyl)tetrasulfide,
2,2'-bis(phenyl methyl methoxysilylethyl)trisulfide,
3,3'-bis(diphenyl isopropoxysilylpropyl)tetrasulfide,
3,3'-bis(diphenyl cyclohexoxysilylpropyl)disulfide,
3,3'-bis(dimethyl ethylmercaptosilylpropyl)tetrasulfide,
2,2'-bis(methyl dimethoxysilylethyl)trisulfide, 2,2'-bis(methyl ethoxypropoxysilylethyl)tetrasulfide,
3,3'-bis(diethyl methoxysilylpropyl)tetrasulfide,
3,3'-bis(ethyl di-sec.butoxysilylpropyl)disulfide,
3,3'-bis(propyl diethoxysilylpropyl)disulfide,
3,3'-bis(butyl dimethoxysilylpropyl)trisulfide,
3,3'-bis(phenyl dimethoxysilylpropyl)tetrasulfide,
3-phenyl ethoxybutoxysilyl 3'-trimethoxysilylpropyl tetrasulfide,
4,4'-bis(trimethoxysilylbutyl)tetrasulfide,
6,6'-bis(triethoxysilylhexyl)tetrasulfide,
12,12'-bis(triisopropoxysilyl dodecyl)disulfide,
18,18'-bis(trimethoxysilyloctadecyl)tetrasulfide,
18,18'-bis(tripropoxysilyloctadecenyl)tetrasulfide,
4,4'-bis(trimethoxysilyl-buten-2-yl)tetrasulfide,
4,4'-bis(trimethoxysilylcyclohexylene)tetrasulfide,
5,5'-bis(dimethoxymethylsilylpentyl)trisulfide,
3,3'-bis(trimethoxysilyl-2-methylpropyl)tetrasulfide,
3,3'-bis(dimethoxyphenylsilyl-2-methylpropyl)disulfide.

The preferred sulfur containing organosilicon compounds which are prepared in accordance with the present invention are the 3,3'-bis(trimethoxy or triethoxy silylpropyl)sulfides. The most preferred compound is 3,3'-bis(triethoxysilylpropyl) tetrasulfide. Therefore as to formula I, preferably Z is

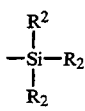

where $R_2$ is an alkoxy of 2 to 4 carbon atoms, with 2 carbon atoms being particularly preferred; Alk is a divalent hydrocarbon of 2 to 4 carbon atoms with 3 carbon atoms being particularly preferred; and n is an integer of from 3 to 5 with 4 being particularly preferred.

As to the compound of formula III, Me is ammonium or an alkali metal. Representative metals include potassium, sodium, rubidium or cesium. Preferably, Me is sodium. Specific examples of compounds of formula III include $Na_2S_2$, $K_2S_2$, $Na_2S_6$, $Cs_2S_2$, $K_2S_2$, $K_2S_3$, $K_2S_2$, $(NH_4)_2S_2$, $(NH_4)_2S_3$, $Na_2S_2$, $Na_2S_3$ and $Na_2S_4$.

As mentioned above, the organosilicon compounds of formula I are prepared by reacting a compound of formula II with a compound of formula III. While the mole ratio of the two reactants may vary, generally speaking, the mole ratio of the compound of formula II to the compound of formula III ranges from about 10:1 to 1:10. Preferably the mole ratio ranges from about 4:1 to 1:4, with a range of from 2:1 being particularly preferred.

The reaction between compound of formula II and the compound of formula III is conducted in the presence of a phase transfer catalyst. Representative phase transfer catalysts may have a quaternary onium cation of the following structural formulae (IV), (V) or (VI):

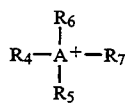 (IV)

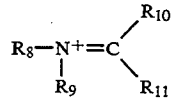 (V)

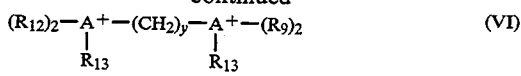 (VI)

wherein A represents nitrogen, phosphorus or arsenic; $R_4$, $R_5$, $R_6$, $R_7$, which may be the same or different, are each a linear or branched chain alkyl radical containing from 1 to 16 carbon atoms, optionally substituted with a phenyl, hydroxyl, halo, nitro, alkoxy or alkoxycarbonyl substituent; a linear or branched chain alkenyl radical containing from 2 to 12 carbon atoms, preferably from 4 to 8 carbon atoms and most preferably an alkenyl radical derived from the starting material conjugated diene; an aryl radical containing from 6 to 10 carbon atoms, optionally substituted by one or more alkyl substituents containing from 1 to 4 carbon atoms or alkoxy, alkoxycarbonyl or halo substituents; and with the proviso that any two of said radicals $R_4$ to $R_7$ may together form a single linear or branched chain alkylene, alkenylene or alkadienylene radical containing from 3 to 6 carbon atoms, $R_8$, $R_9$, $R_{10}$, $R_{11}$, which also may be the same or different, are each a linear or branched chain alkyl radical containing from 1 to 4 carbon atoms; with the proviso that the $R_{10}$, and $R_{11}$ radicals may together form an alkylene radical containing from 3 to 6 carbon atoms; and with the further proviso that the $R_9$ and $R_{10}$ or $R_9$ and $R_{11}$ radicals may together form an alkylene, alkenylene or alkadienylene radical containing 4 carbon atoms and, together with the nitrogen atom, comprising a 5-membered nitrogen heterocycle; $R_{12}$ is a linear or branched chain alkyl radical containing from 1 to 4 carbon atoms, or a phenyl radical; $R_{13}$ is a linear or branched chain alkyl radical containing from 1 to 4 carbon atoms, and which may be the same or different from $R_{12}$, a linear or branched chain alkenyl radical containing from 2 to 12 carbon atoms, preferably from 4 to 8 carbon atoms, and more preferably an alkenyl radical derived from the starting material conjugated diene to be carbonylated; and y is an integer of from 1 to 10, and preferably less than or equal to 6.

Exemplary of the quaternary onium cations having the structural Formula IV, the following are representative: tetramethylammonium, triethylmethylammonium, tributylmethylammonium, trimethyl(n-propyl)ammonium, tetraethylammonium, tetrabutylammonium, dodecyltrimethylammonium, methyltrioctylammonium, heptyltributylammonium, tetrapropylammonium, tetrapentylammonium, tetrahexylammonium, tetraheptylammonium, tetraoctylammonium, tetradecylammonium, butyltripropylammonium, methyltributylammonium, pentyltributylammonium, methyldiethylpropylammonium, ethyldimethylpropylammonium, tetradodecylammonium, tetraoctadecylammonium, hexadecyltrimethylammonium, benzyltrimethylammonium, benzyldimethylpropylammonium, benzyldimethyloctylammonium, benzyltributylammonium, benzyltriethylammonium, phenyltrimethylammonium, benzyldimethyltetradecylammonium, benzyldimethylhexadecylammonium, dimethyldiphenylammonium, methyltrialkyl($C_8$-$C_{10}$) ammonium, methyltriphenylammonium, buten-2-yltriethylammonium, N,N-dimethyltetramethyleneammonium, N,N-diethyltetramethyleneammonium, tetramethylphosphonium, tetrabutylphosphonium, ethyltrimethylphosphonium, trimethylpentylphosphonium, trimethylpentylphosphonium, octyltrimethylphosphonium, dodecyltrimethylphosphonium, trimethylphenylphosphonium, diethyldimethylphosphonium, dicyclohexyldimethylphosphonium, dimethyldiphenylphosphonium, cyclohexyltrimethylphosphonium, triethylmethylphosphonium, methyltri(isopropyl)phosphonium, methyl-tri(n-propyl)phosphonium, methyl-tri(n-butyl)phosphonium, methyl-tri(2-methylpropyl)phosphonium, methyltricyclohexylphosphonium, methyltriphenylphosphonium, methyltribenzyl phosphonium, methyl-tri(4-methylphenyl)phosphonium, methyltrixylylphosphonium, diethylmethylphenylphosphonium, dibenzylmethylphenylphosphonium, ethyltriphenylphosphonium, tetraethylphosphonium, ethyl-tri(n-propyl)phosphonium, triethylpentylphosphonium, hexadecyltributylphosphonium, ethyltriphenylphosphonium, n-butyl-tri(n-propyl)phosphonium, butyltriphenylphosphonium, benzyltriphenylphosphonium, (β-phenylethyl)dimethylphenylphosphonium, tetraphenylphosphonium, triphenyl(4-methylphenyl)phosphonium, tetrakis(hydroxymethyl)phosphonium, tetrakis(2-hydroxyethyl)phosphonium, and tetraphenylarsonium.

And exemplary of the Formula V cations are the following: N-methylpyridinium, N-ethylpyridinium, N-hexadecylpyridinium and N-methylpicolinium.

Among the cations having the structural Formula VI, the following are representative: 1,2-bis(trimethylammonium)ethane, 1,3-bis(trimethylammonium)propane, 1,4-bis(trimethylammonium)butane, and 1,3-bis(trimethylammonium)butane.

Representative of the anions of said onium salts include the following ions: $F^-$, $ClO_4^-$, $PF_6^-$, $BF_4^-$, tetraphenylborate anion, $PO_4^{-3}$, $HPO_4^{-2}$, $H_2PO_4^-$, $CH_3SO_3^-$,

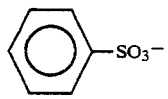

$HSO_4^-$, $NO_3^-$, $SO_4^{-2}$, $CL^-$, and $BR^-$. Preferably, the anion is $Cl^-$.

A particularly preferred onium salt that is used is methyl trialkyl ($C_8-C_{10}$) ammonium chloride which is commercially available under the trademark Adogen ®464 from Sherex Chemical Company of Dublin, Ohio, and from Henkel Corporation, Minneapolis, Minn., under the trademark Aliquot ®336.

The amount of onium salt that is used in the process of the present invention may vary. Generally speaking, the amount of onium salt will range from about 0.1 to 10 mol percent, relative to the compound of formula II, with a range of from 1 to 5 mole percent being preferred.

Wherein the phase transfer catalyst may be added to the reaction at any time, from a practical standpoint, the catalyst is preferably combined with the silane compound of formula II prior to reacting the silane compound with the sulfide compound of formula III.

The process of the present invention uses an aqueous system, however, one may optionally use a two phase aqueous/organic system. In fact, it is preferred to use an aqueous/organic system because the presence of the organic phase assists in the phase separation upon completion of the reaction. When the organic phase is used, preferably the silane compound is predissolved in the organic phase prior to addition to the sulfide compound of formula III. Representative examples of organic solvents include toluene, xylene, benzene, heptane, octane, decane, chlorobenzene and the like.

As mentioned above, the process of the present invention is conducted in the presence of an aqueous phase. The volume of water that is present may vary. Preferably, the sulfide of formula III is substantially dissolved in the aqueous phase prior to reaction with the silane compound of formula II. The concentration of the sulfide in the aqueous phase generally ranges from about 20 to 50 percent by weight. Preferably, the concentration of the sulfide in the aqueous phase ranges from about 25 to 45 percent.

In accordance with the preferred embodiment of the present invention, the sulfide of formula III is dissolved in the aqueous phase. The mixture is then heated, optionally under an inert atmosphere. The mixture may be heated to a temperature ranging from about 60° to 100° C., with a temperature of from 75° to 95° C. being preferred. The silane compound is then added to the aqueous phase. As indicated above the optional organic phase may then be added or the silane can be predissolved in the organic phase along with the appropriate amount of phase transfer catalyst. After the sulfide and silane are combined, the reaction is allowed to continue with mixing. Additional amounts of the organic solvent can then be added to further assist phase separation. Upon filtration, the filtrate is separated into the aqueous phase and organic phase containing the desired product. Any unreacted reagents and/or solvent are removed from the organic phase to yield the desired product.

This invention is illustrated by the following working example which is presented merely for the purpose of illustration and is not intended to be limiting the scope of the invention. Unless specifically indicated otherwise, parts and percentages are given by weight.

EXAMPLE 1

Preparation of 3,3'-bis(triethoxysilylpropyl)tetrasulfide

A 3 liter three necked glass reaction vessel with a mechanical stirrer and nitrogen inlet was initially charged with 240 g (1.0 mole) of sodium sulfide nonahydrate, 96.0 g (3.0 moles) of elemental sulfur and 750 ml of water. The mixture was heated with stirring under a nitrogen atmosphere to 85°–90° C. to form a homogeneous deep red solution of sodium tetrasulfide. Once formed, a solution of 505.5 g (2.1 moles) of (3-chloropropyl)triethoxysilane (CPTES), 25.0 g (0.0538 moles) of Adogen 464 (phase transfer catalyst) and 100 ml of toluene was then charged into the hot sodium tetrasulfide solution over a 15-minute period. Five minutes after the addition had been completed, the color of the mixture markedly lightens. The mixture was allowed to stir an additional 15 minutes before adding 500 ml of toluene. The warm mixture was then filtered to remove a small amount (13.4 g) of an insoluble oligomeric material. The filtrate was then separated into a lower aqueous water-white brine phase and an upper amber-yellow product/toluene phase. The toluene phase was then stripped on a rotary evaporator to remove excess toluene from the product. The crude product was then subjected to a high vacuum stripping to remove any residual toluene and any residual unreacted CPTES. The final weight of the product after stripping was 520 (96.6 weight percent of theory).

Both carbon-13 and proton NMR analyses confirm the structure of the 3,3'-bis(triethoxysilylpropyl) tetrasulfide as compared to known standard materials from commercial sources.

EXAMPLE 2

Preparation of 3,3'-bis(triethoxysilylpropyl)disulfide

A one (1) liter three necked reaction vessel with a mechanical stirrer, reflux condenser, thermometer and N₂ inlet was initially charged with 24 g (0.1 mole) of sodium sulfide nonahydrate, 3.2 g (0.1 mole) of elemental sulfur and 81 ml of water. The mixture was heated with stirring under a nitrogen atmosphere to 85°–90° C. to form a homogeneous deep red solution of sodium disulfide. Once formed, a solution of 38.48 g (0.16 moles) of (3-chloropropyl)triethoxysilane (CPTES) and 55 ml of toluene was added. After the reactants resumed reflux, 5 ml of a mixture of 3 g of Adogen 464 and 27 ml of toluene was added. After 10 minutes, an additional 5 ml of the Adogen 464/toluene mixture was added. Thereafter, a final 5 ml of the Adogen 464/toluene mixture was added. The material was filtered and phase separated into an aqueous phase and a product/toluene phase. The toluene phase was then stripped on a rotary evaporator to remove excess toluene from the product. The crude product was then subjected to a high vacuum stripping to remove any residual toluene and any CPTES. The final weight of the product after stripping was 32.5 g (85.7 weight percent of theory).

Both carbon-13 and proton NMR analyses confirm the structure of the 3,3'-bis(triethoxysilylpropyl)disulfide.

While certain representative embodiment and details have been shown for the purpose of illustrating the invention, it will be apparent to those skilled in the art that various changes and modifications may be made therein without departing from the spirit or scope of the invention.

What is claimed is:

1. A process for the production of organosilicon compounds of the formula $$Z\text{-Alk-}S_n\text{-Alk-}Z \quad (I)$$

in which Z is selected from the group consisting of

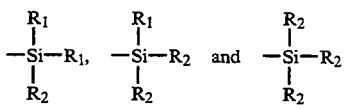

where R₁ is an alkyl group of 1 to 4 carbon atoms, cyclohexyl or phenyl;

R₂ is alkoxy of 1 to 8 carbon atoms, or cycloalkoxy of 5 to 8 carbon atoms;

Alk is a divalent hydrocarbon of 1 to 18 carbon atoms and n is an integer of 2 to 8; comprising reacting (A) a compound of the formula:

$$Z\text{-Alk-}X \quad (II)$$

when X is Cl, Br or I; with (B) a compound of the formula $$Me_2S_n \quad (III)$$

where Me is ammonium, or an alkali metal;
wherein the reaction is conducted in the presence of a phase transfer catalyst and an aqueous phase.

2. The process of claim 1 wherein Z is:

R₂ is an alkoxy of 2 to 4 carbon atoms, n is an integer of from 2 to 4, and Alk is a divalent hydrocarbon of 2 to 4 carbon atoms.

3. The process of claim 1 wherein X is Cl.

4. The process of claim 1 wherein Me is sodium.

5. The process of claim 2 wherein R is an alkoxy of 2 carbon atoms.

6. The process of claim 1 wherein the reaction is carried out at a temperature ranging from 60° C. to 100° C.

7. The process of claim 1 wherein the reaction is conducted in the presence of an aqueous phase and an organic phase.

8. The process of claim 1 wherein the phase transfer catalyst is selected from formulae:

 (IV)

 (V)

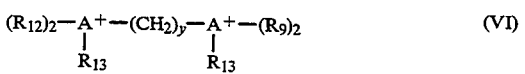 (VI)

wherein A represents nitrogen, phosphorus or arsenic; R₄, R₅, R₆, R₇, which may be the same or different, are each a linear or branched chain alkyl radical containing from 1 to 16 carbon atoms, may be substituted with a phenyl, hydroxyl, halo, nitro, alkoxy or alkoxycarbonyl substituent; a linear or branched chain alkenyl radical containing from 2 to 12 carbon atoms; an aryl radical containing from 6 to 10 carbon atoms, may be substituted by one or more alkyl substituents containing from 1 to 4 carbon atoms or alkoxy, alkoxycarbonyl or halo substituents; and with the proviso that any two of said radicals R₄ to R₇ may together form a single linear or branched chain alkylene, alkenylene or alkadienylene radical containing from 3 to 6 carbon atoms, R₈, R₉, R₁₀, R₁₁, which also may be the same or different, are each a linear or branched chain alkyl radical containing from 1 to 4 carbon atoms; with the proviso that the R₁₀ and R₁₁ radicals may together form an alkylene radical containing from 3 to 6 carbon atoms; and with the further proviso that the R₉ and R₁₀ or R₉ and R₁₁ radicals may together form an alkylene, alkenylene or alkadienylene radical containing 4 carbon atoms and, together with the nitrogen atom, comprising a 5-membered nitrogen heterocycle; R₁₂ is a linear or branched chain alkyl radical containing from 1 to 4 carbon atoms, or a phenyl radical; R₁₃ is a linear or branched chain alkyl radical containing from 1 to 4 carbon atoms, and which may be the same or different from R₁₂, a linear or branched chain alkenyl radical containing from 2 to 12 carbon atoms; and y is an integer greater than or equal to 1 and less than or equal to 10.

9. The process of claim 8 wherein said phase transfer catalyst is selected from the group of cations consisting of tetramethylammonium, triethylmethylammonium, tributylmethylammonium, trimethyl(n-propyl)ammonium, tetraethylammonium, tetrabutylammonium, dodecyltrimethylammonium, methyltrioctylammonium, heptyltributylammonium, tetrapropylammonium, tetrapentylammonium, tetrahexylammonium, tetraheptylammonium, tetraoctylammonium, tetradecylammonium, butyltripropylammonium, methyltributylammonium, pentyltributylammonium, methyldiethylpropylammonium, ethyldimethylpropylammonium, tetradodecylammonium, tetraoctadecylammonium, hexadecyltrimethylammonium, benzyltrimethylammonium, benzyldimethylpropylammonium, benzyldimethyloctylammonium, benzyltributylammonium, benzyltriethylammonium, phenyltrimethylammonium, benzyldimethyltetradecylammonium, benzyldimethylhexadecylammonium, dimethyldiphenylammonium, methyltrialkyl($C_8$–$C_{10}$) ammonium, methyltriphenylammonium, buten-2-yltriethylammonium, N,N-dimethyltetramethyleneammonium, N,N-diethyltetramethyleneammonium, tetramethylphosphonium, tetrabutylphosphonium, ethyltrimethylphosphonium, trimethylpentylphosphonium, trimethylpentylphosphonium, octyltrimethylphosphonium, dodecyltrimethylphosphonium, trimethylphenylphosphonium, diethyldimethylphosphonium, dicyclohexyldimethylphosphonium, dimethyldiphenylphosphonium, cyclohexyltrimethylphosphonium, triethylmethylphosphonium, methyltri(isopropyl)phosphonium, methyl-tri(n-propyl)phosphonium, methyl-tri(n-butyl)phosphonium, methyl-tri(2-methylpropyl)phosphonium, methyltricyclohexylphosphonium, methyltriphenylphosphonium, methyltribenzyl phosphonium, methyl-tri(4-methylphenyl)phosphonium, methyltrixylylphosphonium, diethylmethylphenylphosphonium, dibenzylmethylphenylphosphonium, ethyltriphenylphosphonium, tetraethylphosphonium, ethyl-tri(n-propyl)phosphonium, triethylpentylphosphonium, hexadecyltributylphosphonium, ethyltriphenylphosphonium, n-butyl-tri(n-propyl)phosphonium, butyltriphenylphosphonium, benzyltriphenylphosphonium, (β-phenylethyl)dimethylphenylphosphonium, tetraphenylphosphonium, triphenyl(4-methylphenyl)phosphonium, tetrakis(hydroxymethyl)phosphonium, tetrakis(2-hydroxyethyl)phosphonium, tetraphenylarsonium, N-methylpyridinium, N-ethylpyridinium, N-hexadecylpyridinium, N-methylpicolinium, 1,3-bis-2-yldimethylammonium)propane, 1,2-bis(trimethylammonium)ethane, 1,3-bis(trimethylammonium)propane, 1,4-bis(trimethylammonium)butane, and 1,3-bis(trimethylammonium)butane and selected from the group of anions consisting of $F^-$, $ClO_4^-$, $PF_6^-$, $BF_4^-$, tetraphenylborate anion, $PO_4^{-3}$, $HPO_4^{-2}$, $H_2PO_4^-$, $CH_3SO_3^-$,

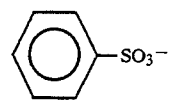

$HSO_4^-$, $NO_3^-$, $SO_4^{-2}$, $Cl^-$, and $Br^-$.

10. The process of claim 1 wherein said phase transfer catalyst is methyl trialkyl ($C_8$–$C_{10}$) ammonium chloride.

11. The process of claim 1 wherein said phase transfer catalyst is an onium salt that is present in an amount ranging from 0.1 to 10 mol percent relative to the compound of formula II.

12. The process of claim 7 wherein an organic solvent is selected from the group consisting of toluene, xylene, benzene, heptane, octane, decane, chlorobenzene and the like.

13. The process of claim 12 wherein said organic solvent is toluene.

* * * * *